Figure 1:
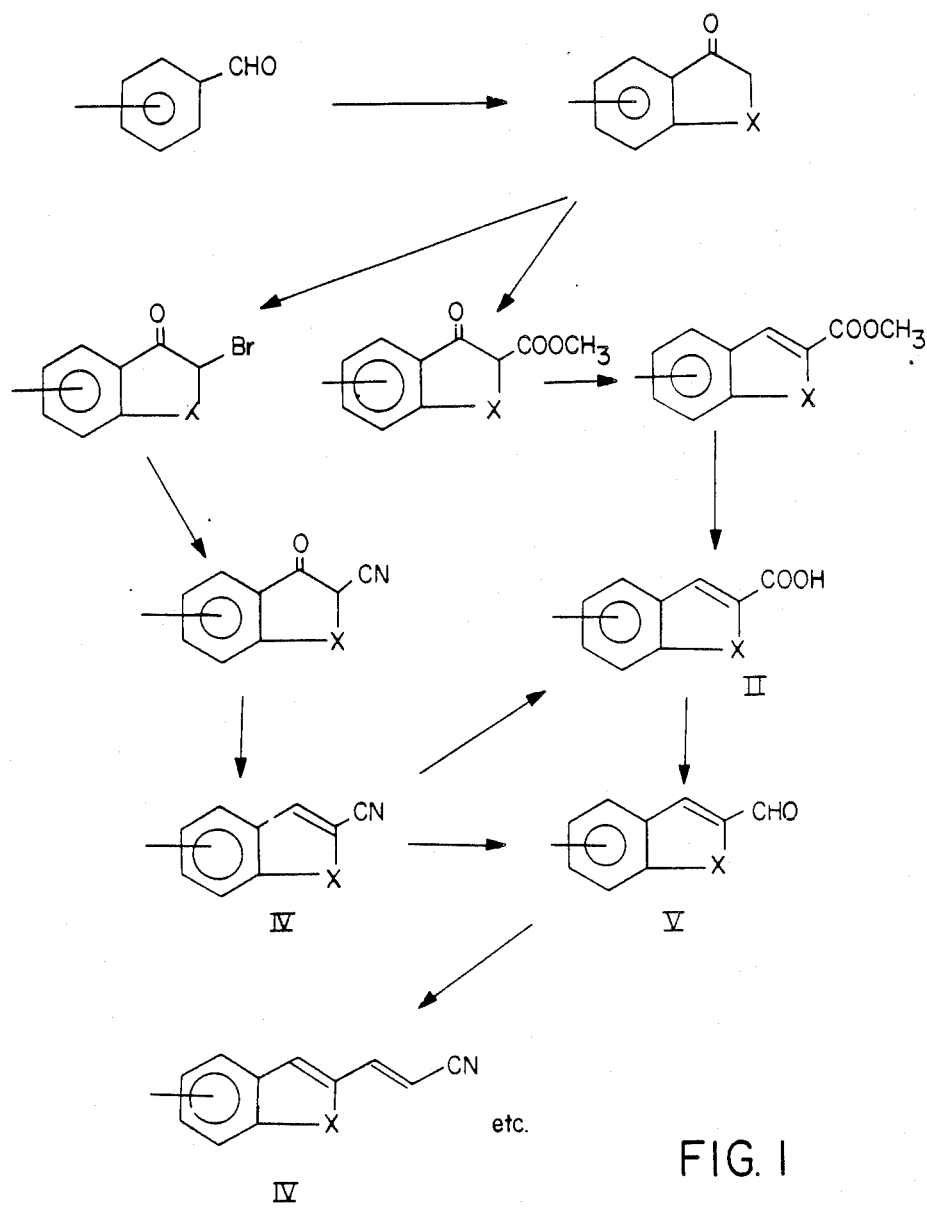
Figure 2:
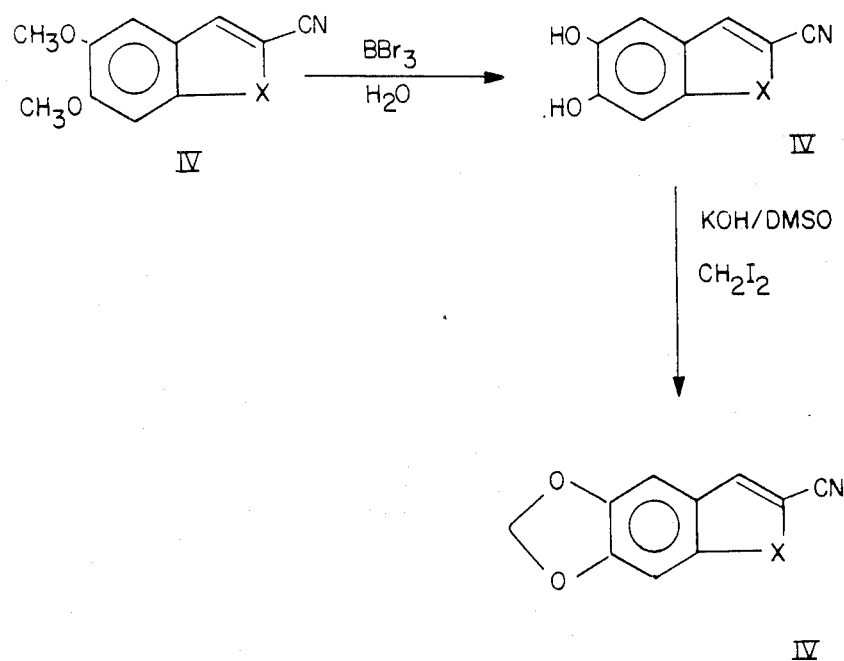

United States Patent [19]

Logan et al.

[11] Patent Number: 4,705,782

[45] Date of Patent: Nov. 10, 1987

[54] INDENE AND NAPHTHALENE DERIVATIVES

[75] Inventors: Robert T. Logan, Lanark; James Redpath, Bishopbriggs-Glasgow; Robert G. Roy, Larkhall, all of Scotland

[73] Assignee: Akzo N.V., Arnhem, Netherlands

[21] Appl. No.: 844,146

[22] Filed: Mar. 26, 1986

[30] Foreign Application Priority Data

Apr. 2, 1985 [GB] United Kingdom ............... 8508588

[51] Int. Cl.$^4$ .................. C07C 93/10; C07C 131/00; A61K 31/05; A61K 31/155
[52] U.S. Cl. ........................... 514/150; 260/500.5 H; 514/463; 514/575; 549/433; 564/228; 564/229
[58] Field of Search ............... 260/500.5 H; 564/228, 564/229; 549/433; 514/150, 463, 575

[56] References Cited

U.S. PATENT DOCUMENTS

| | | | |
|---|---|---|---|
| 3,130,232 | 4/1964 | Paquette | 564/228 |
| 3,530,165 | 9/1970 | Aldrich et al. | 260/500.5 H |
| 3,560,519 | 2/1971 | Burk et al. | 260/500.5 H |
| 3,829,467 | 8/1974 | Diamond et al. | 260/500.5 H |
| 4,018,817 | 4/1977 | Noguchi et al. | 260/500.5 H |
| 4,139,555 | 2/1979 | Zerbes | 564/228 |
| 4,272,547 | 6/1981 | Haas et al. | 260/500.5 H |
| 4,325,964 | 4/1982 | Lafon | 260/500.5 H |
| 4,604,407 | 8/1986 | Haslanger et al. | 260/500.5 H |
| 4,605,669 | 8/1986 | Summers | 260/500.5 H |
| 4,608,390 | 8/1986 | Summers | 260/500.5 H |

FOREIGN PATENT DOCUMENTS 304441 1/1929 United Kingdom .
2001956 2/1979 United Kingdom .

Primary Examiner—J. E. Evans
Attorney, Agent, or Firm—William M. Blackstone

[57] ABSTRACT

The invention relates to compounds of the general formula I

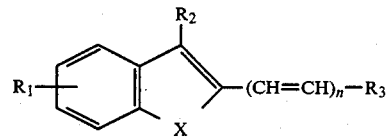

wherein
$R_1$ represents one up to and including four, the same or different substituents selected from alkyl(1–6 C), alkoxy(1–6 C), hydroxy, halogen, $NO_2$, $CF_3$ or the group $-NR_5R_6$,
whereby two substituents taken together may also represent a methylene-dioxy group,
X represents a member selected from

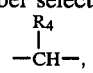

$-CH_2-CH_2-$ and $-CH=CH-$,
n has the value 0, 1 or 2,
$R_3$ represents one of the moieties:

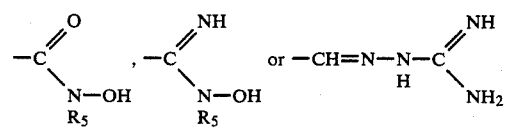

and
$R_2$, $R_4$, $R_5$ and $R_6$ represent hydrogen or alkyl(1–6 C), and pharmaceutically acceptable salts thereof, suitable in the treatment of heartfailure.

6 Claims, 2 Drawing Figures

FLOW CHART

FLOW CHART

INDENE AND NAPHTHALENE DERIVATIVES

The invention relates to compounds of the general formula I

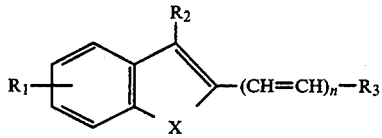

wherein
R$_1$ represents one up to and including four, the same or different substituents selected from alkyl(1-6 C), alkoxy(1-6 C), hydroxy, halogen, NO$_2$, CF$_3$ or the group —NR$_5$R$_6$,
whereby two substituents taken together may also represent a methylene-dioxy group,
X represents the group

—CH$_2$—CH$_2$— or —CH=CH—,
n has the value 0, 1 or 2,
R$_3$ represents one of the moieties:

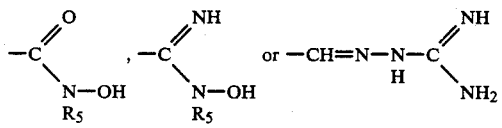

and
R$_2$, R$_4$, R$_5$ and R$_6$ represent H or alkyl(1-6 C) and pharmaceutically acceptable salts thereof.

The compounds according to the invention have a cardiotonic activity and more particularly they show a very potent increase of the force and energy of the heart-muscular contractions (positive inotropic effect).

The compounds of the invention may be prepared by any method known for the preparation of analogous compounds.

A very suitable starting product for the preparation of the compounds I is a compound of the formula II

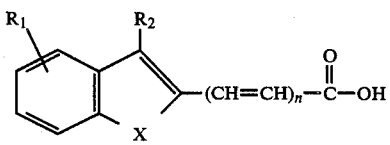

wherein
R$_1$, , R$_2$, n and X have the aforesaid meanings.

Compounds of the invention in which R$_3$ represents the moiety

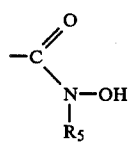

may for example be prepared by reacting the compound of formula II or an acid halide or anhydride thereof with an hydroxylamine of the formula:

in which
R$_5$ has the aforesaid meaning, or a reactive derivative thereof, in which the hydrogen atom is replaced by a more reactive moiety, such as an alkali metal.

Compounds of the invention in which R$_3$ represents a

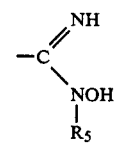

moiety may, for example, be prepared from a nitrile of the general formula IV:

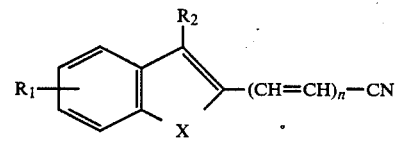

in which R$_1$, R$_2$, X and n have the meanings assigned before by reacting the said nitrile in the usual manner with a compound of the formula:

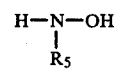

wherein R$_5$ has the aforesaid meanings, or a reactive derivative thereof, in which hydrogen (at the nitrogen atom) has been replaced by a more reactive moiety, such as an alkali metal.

The nitrile of formula IV may be prepared in the usual manner from the corresponding carboxylic acid of formula II by converting the carboxylic acid into the corresponding carboxamide followed by dehydration of the carboxamide.

Compounds of the invention, in which R$_3$ represents a —C=N—NH—C(=NH)NH$_2$ moiety, may most conveniently be prepared from an aldehyde of the formula:

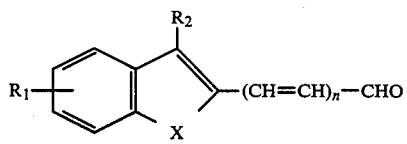

by condensation of this compound (V) with amino guanidine or a salt thereof.

The aldehyde of formula V can be prepared in various manners. For example the aldehyde may be manufactured by reducing the carboxylic acid of formula II in a well known manner.

Another convenient synthesis for preparing the aldehyde consists of a mild reduction of the corresponding nitrile of formula II, e.g. with the aid of a metal hydride such as diisobutylaluminiumhydride.

The starting product of general formula II may be prepared by known methods. The attached flow sheet shows the preparation of a compound of formula II, wherein n=0. Chain length extension to n=1 and n=2 can be obtained by converting the carboxylic acid II (n=0) into the corresponding aldehyde (n=0) and reacting said aldehyde with the appropriate phosphonate ylid using reaction conditions well known in carrying out the Witting reaction.

Appropriate phosphonate ylids are, for example, cyanomethylene triphenylphosphorane, carboxymethylene triphenylphosphorane and corresponding (alkyl)esters, and 3-cyano propen(2)-ylidene triphenylphosphorane. If necessary, the nitrile—obtained through this Wittig reaction—can be converted into the corresponding amide or carboxylic acid.

Preferably most substituents at the benzoring (see $R_1$) are already present in one of the starting products. Nevertheless it is very well possible to convert a substituent $R_1$ into another substituent $R_1$ after the above mentioned condensation reactions.

Thus, one or more hydroxy groups ($R_1$) may be converted into the corresponding alkoxy groups or halogen in the usual manner. Furthermore two hydroxy groups may be converted into one methylene-dioxy group and an alkoxy group may be hydrolysed to the corresponding hydroxy group.

The compounds according to the general formula I may be converted into a pharmaceutically acceptable salt.

The compounds of formula I which have an alkaline character may be obtained as the free base or as an acid addition salt. If required, however, the free base I can be prepared from the salt, for example by reaction with an alkaline compound or by means of an ion exchanger, whilst the free base I can be converted in a simple manner into an acid addition salt.

Pharmaceutically acceptable acid addition salts are derived from acids, such as hydrochloric acid, sulphuric acid, phosphoric acid, acetic acid, propionic acid, glycolic acid, maleic acid, fumaric acid, malonic acid, succinic acid, tartaric acid, lactic acid, citric acid, ascorbic acid, salicylic acid, benzoic acid and methanesulphonic acid.

Compounds I having an acidic nature may be converted into a metal salt, preferably an alkali metal salt such as the sodium salt.

By the term "alkyl(1-6 C)" as used in the definitions of $R_1$, $R_4$, $R_5$ and $R_6$ is meant a saturated hydrocarbon with 1 to 6 carbon atoms, and preferably 1 to 4 carbon atoms, such as methyl, ethyl, propyl, isopropyl, butyl, isobutyl, tert.butyl, pentyl and isopentyl.

An alkoxy(1-6 C) group is an alkyloxy group, in which the term alkyl has a similar meaning as above.

By halogen in the definition of $R_1$ is preferably meant iodine, bromine, chlorine and fluorine. The most preferred halogens are chlorine and bromine.

The said compounds in accordance with the invention can be administered either orally, locally or parenterally, preferably in a daily dose between 0.01 and 50 mg/kg body weight. For this purpose the compounds are processed in a form suitable for oral, local or parenteral administration, for example a tablet, pill, capsule, solution, suspension, emulsion, paste or spray. The oral form is the most preferred form of administration.

The most potent inotropic compounds are found amongst those compounds of formula I in which at least two substituents $R_1$ are present selected from hydroxy or alkoxy or in which at least one methylene-dioxy group ($R_1$) is present, whereby the dimethoxy or methoxy-hydroxy substitution pattern is most preferred.

Preferred compounds of formula I are moreover those compounds I in which X is —$CH_2$—$CH_2$—.

The position of the double bond between nitrogen and carbon in some of the moieties defined by $R_3$ of formula I cannot be clearly specified, because an equilibrium will prevail between:

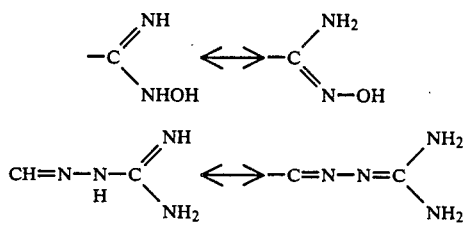

The preferred $R_3$ moiety in the compounds of the invention is the N-hydroxy-(carbox)imidamide moiety.

The preferred value of n is 0 or 1.

EXAMPLE 1

A. 2-Bromo-5,6-dimethoxy-indan-1-one 5,6-Dimethoxyindan-1-one (50 g) was dissolved in chloroform (1040 ml) and ethanol (1040 ml) and the solution was stirred and heated to 50° C. then treated portionwise over 7 hours with cupric bromide (104 g). After a further 16 hours at 50° C. the suspension was cooled and the precipitated cuprous bromide was filtered off. The filtrate was washed with saturated potassium bicarbonate solution, brine, then dried over magnesium sulphate, filtered, evaporated to low volume and triturated with diethyl ether. The resultant yellow solid was filtered and dried at 60° C. under vacuum to give 2-bromo-5,6-dimethoxy-indan-1-one (69.3 g), m.p. 159°–160° C.

B. 2-Cyano-5,6-dimethoxy-indan-1-one

2-Bromo-5,6-dimethoxy-indan-1-one (69.1 g) was suspended in ethanol (1,200 ml) and added to a solution of potassium cyanide (70.4 g) in water (2,200 ml). The reaction mixture was heated at reflux for 1 hour and then the ethanol was distilled off. The dark solution was cooled, stirred and carefully neutralised with hydrochloric acid (5M, 120 ml) in a well ventilated hood. The organic extracts were combined, washed with brine, dried over magnesium sulphate, filtered, then concentrated to low volume under reduced pressure. The residual liquid was filtered through a column of coarse silica (0.2–0.5 mm, Merck, 300 g) and the column was eluted with dichloromethane. The appropriate fractions were combined and evaporated to dryness to give 2-Cyano-5,6-dimethoxy-indan-1-one (24.6 g). A portion crystallised from dichloromethane: ether; m.p. 177°–179° C.

C. 5,6-Dimethoxy-1H-indene-2-carbonitrile

2-Cyano-5,6-dimethoxy-indan-1-one (18.2 g) was suspended in ethanol (360 ml) under an atmosphere of nitrogen and treated with a solution of sodium borohydride (6.57 g) in water (25 ml) and ethanol (36 ml). After 1½ hours dichloromethane (200 ml) was added. After a further 30 minutes the excess sodium borohydride was destroyed by the dropwise addition of acetic acid (2 ml) in dichloromethane (10 ml). The inorganic salts were filtered off and the filtrate was concentrated under reduced pressure then extracted into ethyl acetate (3×200 ml). The organic extracts were combined, washed with brine, dried over magnesium sulphate, filtered and evaporated to dryness to give 2-hydroxy-5,6-dimethoxyindane-2-carbonitrile as a yellow solid (17.1 g).

The crude alcohol (17.1 g) was suspended in hydrochloric acid (5M, 170 ml) and the mixture was stirred and heated to 75° C. After 30 min. the dark solution was cooled in an ice-bath and the resultant green solid was filtered off and dried at 60° C. The product was dissolved in dichloromethane and the solution was passed through a column of coarse silica (0.2–0.5 mm, Merck, 80 g). The appropriate fractions were combined and evaporated to dryness to give 5,6-dimethoxy-1H-indene-2-carbonitrile (12.6 g), m.p. 140°–141° C.

D.
N-hydroxy-5,6-dimethoxy-1H-indene-2-carboximidamide hydrochloride salt Sodium metal (1.86 g) was cut into small pieces and added to a stirred methanol solution (30 ml) under an atmosphere of nitrogen. When all the sodium had dissolved the hot solution was treated with a warm solution of hydroxylamine hydrochloride (5.65 g) in methanol (40 ml). After 1 hour the white suspension of sodium chloride was filtered off and the filtrate was added to 5,6-dimethoxy-1H-indene-2-carbonitrile (5.5 g). The solution was stirred at 50° C. for 3 hours then cooled, diluted with water (400 ml), stirred and the white solid filtered and dried to give crude N-hydroxy-5,6-dimethoxy-1H-indene-2-carboximidamide. The free base was dissolved in methanol (120 ml), stirred, and the solution was saturated with hydrogen chloride gas. After 5 min. the solution was concentrated, diluted with ether and the white solid was filtered. Recrystallisation from methanol:ether (1:2) afforded pure N-hydroxy-5,6-dimethoxy-1H-indene-2-carboximidamide hydrochloride (6.2 g), m.p. 220°–229° C. (dec.).

EXAMPLE 2
N-hydroxy-5,6-dimethoxy-N-methyl-1H-indene-2-carboximidamide hydrochloride salt Sodium metal (0.40 g) was cut into small pieces and added to a stirred solution of methanol (30 ml) under an atmosphere of nitrogen. When all the sodium had dissolved the solution was treated with a solution of N-methylhydroxylamine HCl (1.45 g) in methanol (30 ml). After 30 minutes the white suspension of sodium chloride was filtered off and the filtrate was added to 5,6-dimethoxy-1H-indene-2-carbonitrile (3.6 g). The resultant solution was stirred and heated at reflux for 5 hours then evaporated to dryness.

The residue was chromatographed through a column of coarse silica (0.2–0.5 mm, Merck, 150 g) in dichloromethane:methanol (85:15 v/v). The appropriate fractions were combined and evaporated to dryness to give N-hydroxy-5,6-dimethoxy-N-methyl-1H-indene-2-carboximidamide as a white solid (3.2 g). The free base was dissolved in ethyl alcohol (25 ml) and dichloromethane (25 ml) then treated with a solution of dry ether (200 ml) saturated with HCl gas. The precipitated yellow solid was filtered and recrystallised from ethyl alcohol to give N-hydroxy-5,6-dimethoxy-N-methyl-1H-indene-2-carboximidamide hydrochloride (2.6 g), m.p. 176°–182° C. (decomp.).

EXAMPLE 3
A. 5,6-Dimethoxy-1H-indene-2-carboxaldehyde 5,6-Dimethoxy-1H-indene-2-carbonitrile (1.8 g) was suspended in dry toluene (40 ml) under an atmosphere of nitrogen. The reaction mixture was cooled to −5° C. and treated dropwise with a solution of diisobutylaluminium hydride in toluene (1.5M, 13 ml). After 30 minutes the solution was treated with methanol (5 ml) then poured into hydrochloric acid (1M, 200 ml) and stirred for 15 minutes. The resultant solution was extracted into dichloromethane (4×100 ml) then the organic extracts were combined, washed with brine, dried over magnesium sulphate and evaporated to dryness. The residue (1.4 g) was crystallised from dichloromethane:ether to give 5,6-dimethoxy-1-H-indene-2-carboxaldehyde as a white solid, m.p. 125°–128° C.

B.
3-(5,6-Dimethoxy-1H-indene-2-yl)-2-propenenitrile

Cyanomethylene-triphenylphosphorane was prepared according to the method of S. Trippett and D. M. Walker [J.C.S., 1959, 3874–3876] and S. S. Novikov and G. A. Shvekhgeimer [C.A., 1961, 55, 13353 g]. A mixture of 5,6-dimethoxy-1H-indene-2-carboxaldehyde (7.50 g) and cyanomethylene triphenylphosphorane (22.06 g) in dry toluene (270 ml) was stirred and heated to reflux for 1 hour. The reaction mixture was then evaporated to dryness and the residue was dissolved in a mixture of dichloromethane (50 ml) and toluene (50 ml) and passed through a column of coarse silica (0.2–0.5 mm, Merck, 600 g). The column was eluted with toluene:ethyl acetate (4:1 v/v). The appropriate fractions were combined and evaporated to dryness and the residue was crystallised from dichloromethane:diethyl ether to give pure (E)-3-3-(5,6-dimethoxy-1H-indene-2-yl)-2-propenenitrile (7.01 g), m.p. 133°–134° C.

C.
N-hydroxy-3-(5,6-dimethoxy-1H-indene-2-yl)-prop-2-ene-imidamide hydrochloride Using the procedure described in Example 1 (E)-3-(5,6-dimethoxy-1H-indene-2-yl)-2-propenenitrile was converted into (E)-N-hydroxy-3-(5,6-dimethoxy-1H-indene-2-yl)-prop-2-ene-imidamide hydrochloride, m.p. 170° C. (dec.).

EXAMPLE 4
5,6-Dimethoxy-1H-indene-2-carboxaldehyde-aminoiminomethyl hydrazone hydrochloride Aminoguanadinium hydrogen carbonate (2.5 g) was suspended in methanol (35 ml) and the mixture was treated with 5M hydrochloric acid until all the solid had dissolved. The resultant solution was added to a suspension of 5,6-dimethoxy-1H-indene-2-carboxaldehyde (3.7 g) in ethanol (40 ml) and the mixture was stirred at room temperature for 16 hours under an atmosphere of nitrogen. The white suspension was then diluted with diethyl (250 ml) and the white solid was filtered and dried to give 5,6-dimethoxy-1H-indene-2-carboxaldehyde-amino-iminomethyl hydrazone hydrochloride (4.9 g). A portion crystallised from methanol:acetone had m.p. 261° C. (dec.).

EXAMPLE 5

A. 1,2-Dihydro-N-hydroxy-6,7-dimethoxy naphthalene-3-carboxamide

Hydroxylamine hydrochloride (5.3 g) was dissolved in warm ethanol (100 ml). The solution was stirred under an atmosphere of nitrogen and treated with a warm solution of potassium hydroxide (6.4 g) in ethanol (50 ml). After 10 min. a solution of 10 g of 1,2-dihydro-6,7-dimethoxy-naphthalene-3-carboxylic acid ethyl ester (Org. Synthesis 26, 28, 1946) in ethanol (250 ml) was added and the resultant mixture was allowed to stand at room temperature for 72 hours. The resultant suspension was filtered to remove the precipitated potassium chloride and the filtrate was evaporated to dryness.

The resultant yellow residue was dissolved in water (250 ml), filtered and the filtrate was acidified with 5M hydrochloric acid. The precipitated product was filtered and dried at 65° C. under vacuum to give 1,2-dihydro-N-hydroxy-6,7-dimethoxy-naphthalene-3-carboxamide (8.1 g). A portion crystallised from acetone, m.p. 179°–180° C.

B. 1,2-Dihydro-N-hydroxy-6,7-dimethoxy-naphthalene-3-carboxamide sodium salt 1,2-Dihydro-N-hydroxy-6,7-dimethoxy-naphthalene-3-carboxamide (2.5 g) was added to a stirred solution of sodium metal (0.227 g) in methanol (55 ml). After 15 min. the solution was evaporated to dryness and the residue crystallised from methanol:ether to give 2.5 g of the title product.

EXAMPLE 6

In an analogous manner as described in Example 1 were prepared:

1,2-dihydro-N-hydroxy-6,7-dimethoxy-naphthalene-3-carboximidamide.HCl, m.p. 202°–205° C.

1,2-dihydro-N,6,7-trihydroxy-naphthalene-3-carboximidamide.HCl, m.p. 183°–185° C.

N-Hydroxy-6,7-dimethoxy-naphthalene-2-carboximidamide.HCl, m.p. 203°–208° C.

N,6,7-trihydroxy-naphthalene-2-carboximidamide.HCl, m.p. 238°–243° C.

EXAMPLE 7

In an analogous manner as described in Example 3 is prepared:

(E)-N-hydroxy-3-(1,2-dihydro-6,7-dimethoxy-naphthalen-3-yl)prop-2-ene imidamide.HCl, m.p. 199°–203° C.

EXAMPLE 8

In an analogous manner as described in Example 4 is prepared:

1,2-dihydro-6,7-dimethoxy-naphthalene-3-carboxaldehyde amino-iminomethyl hydrazone.HCl.

We claim:

1. Indene and naphthalene derivatives of the formula I

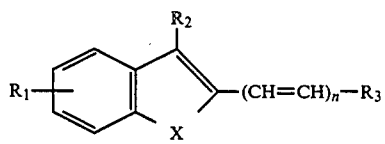

wherein $R_1$ represents one up to and including four, the same or different substituents selected from alkyl (1–6 C), alkoxy (1–6 C), hydroxy, halogen, $NO_2$, $CF_3$ or the group $-NR_5R_6$, whereby two substituents taken together may also represent a methylene dioxy group, X represents the group $-CH-$ or $-CH_2-CH_2-$, n has the value 0, 1 or 2, $R_3$ represents one of the moieties:

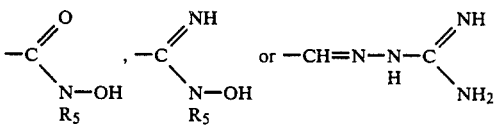

and $R_2$, $R_4$, $R_5$, and $R_6$ represent hydrogen or alkyl (1–6 C), and pharmaceutically acceptable salts thereof.

2. Compound according to claim 1, in which X represents $-CH_2-CH_2-$.

3. Compound according to claim 1, in which $R_1$ represents at least two oxygen bearing substituents selected from alkoxy and hydroxy or in which $R_1$ represents a methylene dioxy group.

4. Compound according to claim 3, in which $R_1$ represents a dimethoxy or a hydroxy-methoxy substitution pattern.

5. Pharmaceutical preparation having a positive inotropic effect comprising an effective amount of a compound according to claim 1 in admixture with a pharmaceutically acceptable carrier.

6. The compound according to claim 1:

1,2-dihydro-N-hydroxy-6,7-dimethoxy-naphthalene-3-carboximidamide and pharmaceutically acceptable salts thereof.

* * * * *